(12) United States Patent
Zappala

(10) Patent No.: US 6,881,184 B2
(45) Date of Patent: Apr. 19, 2005

(54) ABSORBABLE PUBOVAGINAL SLING SYSTEM AND METHOD

(76) Inventor: Stephen M. Zappala, 98 Rattlesnake Hill Rd., Andover, MA (US) 01810

( * ) Notice: Subject to any disclaimer, the term of this patent is extended or adjusted under 35 U.S.C. 154(b) by 0 days.

(21) Appl. No.: 10/196,462

(22) Filed: Jul. 16, 2002

(65) Prior Publication Data
US 2004/0015044 A1 Jan. 22, 2004

(51) Int. Cl.[7] .......................... A61B 17/00; A61B 19/00; A61F 2/02
(52) U.S. Cl. ........................................................ 600/29
(58) Field of Search ............. 600/29–32; 128/DIG. 25, 128/898; 606/228–233

(56) References Cited

U.S. PATENT DOCUMENTS

| 4,938,760 A | * | 7/1990 | Burton et al. ................. 600/29 |
| 5,582,188 A | * | 12/1996 | Benderev et al. ........... 128/898 |
| 5,686,090 A | * | 11/1997 | Schilder et al. ............. 424/423 |
| 6,042,534 A | * | 3/2000 | Gellman et al. .............. 600/30 |
| 6,117,067 A | * | 9/2000 | Gil-Vernet .................... 600/30 |
| 6,306,079 B1 | * | 10/2001 | Trabucco ...................... 600/30 |
| 2002/0151762 A1 | * | 10/2002 | Rocheleau et al. ........... 600/30 |
| 2003/0023137 A1 | * | 1/2003 | Gellman ....................... 600/30 |

* cited by examiner

Primary Examiner—Samuel G. Gilbert
(74) Attorney, Agent, or Firm—Jennifer E. Haeckl, Esq.; Mirick, O'Connell, DeMallie & Lougee, LLP

(57) ABSTRACT

An absorbable pubovaginal sling system for surgical management of urinary incontinence, generally comprising: a latex-free, synthetic sling made entirely of absorbable materials of which at least one of the materials is adapted to stimulate fibroblast interposition; and a looped monofilament suture that is adapted to be transposed to the suprapubic position, supported by an external adjustable tension device, and connected to said sling.

16 Claims, 4 Drawing Sheets

ABSORBABLE PUBOVAGINAL SLING SYSTEM AND METHOD

FIELD OF THE INVENTION

The invention relates to novel systems and methods for surgically managing urinary incontinence that feature an absorbable pubovaginal sling and an external tension adjuster.

BACKGROUND OF THE INVENTION

The pubovaginal sling has gained widespread acceptance in the surgical management of stress urinary incontinence. The surgical procedure has undergone several modifications in an attempt to improve clinical outcomes including modifying the sling material to include, in whole or in part, synthetic, homologous, autologous, or porcine materials; altering the location of the suspension anchor among suprapubic, retropubic, and bone locations; and modifying the surgical position of the sling.

It is apparent that a very delicate balance exists between urinary incontinence and retention, regardless of the sling material employed or the location of the sling suspension. Indeed, the primary factor to predict clinical success is related to the sling tension at the mid-urethra/bladder neck/ sphincteric mechanism. If the tension of the pubovaginal sling is too loose, incontinence persists. If the sling is too tight at the bladder neck, urinary retention will develop. Previous attempts to regulate sling tension have not proven successful and the recommendation for sling tension is for surgeons to utilize "clinical judgment". However, once the surgeon sets the tension during surgery, the tension cannot be adjusted after the surgery is completed.

In addition, recent data suggests that after an extended period of time, the suspension suture is indeed redundant because of the perivesical fibrosis that anchors the bladder into its fixed, high retropubic position. Moreover, the sling itself serves as a matrix for fibroblast deposition, which strengthens and supports the anterior vaginal wall.

Furthermore, since urinary incontinence is not a life threatening condition, many patients are expressing concern and reluctance about conventional procedures that employ materials harvested from cadaveric, bovine and porcine sources.

SUMMARY OF THE INVENTION

It is therefore a primary object of this invention to provide a system and method for managing urinary incontinence that is synthetic, absorbable and does not introduce immune risks into the patient.

It is a further object of this invention to provide an absorbable pubovaginal sling that is adapted to increase the rigidity of the anterior vaginal wall and to improve the integrity of the sphincteric mechanism.

It is a further object of the invention to provide an absorbable sling that is implanted using a surgical technique that is incision free and provides a removeable, patient-controlled tension adjuster to adjust the suture tension of the sling.

A preferred embodiment of the absorbable pubovaginal sling system, for surgical management of urinary incontinence that is adapted to promote increased rigidity of the anterior vaginal wall and improved integrity of the sphincteric mechanism, generally comprises: a latex-free, synthetic sling made entirely of absorbable materials of which at least one of the materials is adapted to stimulate fibroblast interposition; and a monofilament suture that is adapted to be transposed to the suprapubic position. The system preferably further comprises an external adjustable tension device that is connected to said suture and is adapted to support said sling.

One or more of the absorbable materials may be selected from a group consisting of chromic gut, polyglactin, polydioxanone, and combinations thereof; and the monofilament suture is preferably looped and may comprise one or both prolene and nylon.

The sling system may be prefabricated and preferably does not require physician reconstitution. The sling is preferably fibrogenic and either braided or woven with a plurality of fenestrations to allow ingrowth of fibroblasts and deposition of collagen and is preferably adapted to be absorbed at a slow rate. The preferred period of absorption is about 90 days.

The suture is adapted to pass through a patient's subcutaneous tissue and skin to connect to an external adjusting device; wherein the external adjusting device may comprise one or more apertures through which the suture is passed and secured at an adjustable tension. The tension of the suture may be readjusted by opening the apertures of the device to stretch and tighten the suture, and then closing the apertures to secure the suture at the readjusted tension.

Another preferred embodiment of the pubovaginal sling system for surgical management of urinary incontinence in a patient, generally comprises: one or more synthetic slings; one or more monofilament sutures that is connected to the sling and is adapted to be transposed to a suprapubic position; and one or more external adjustable tension devices that is adapted to support the sling by passing the suture through the patient's subcutaneous tissue and out through the patient's skin; threading the suture through the tension device; tightening the tension of the suture until a desired level of tension support is achieved; and at least temporarily fixing the suture at the desired level of tension support with the tension device.

A preferred method of the invention for surgically managing urinary incontinence in a patient, generally comprises the steps of: providing one or more pubovaginal slings; providing one or more monofilament sutures that is connected to the sling and is adapted to be transposed to a suprapubic position; providing one or more external adjustable tension devices; passing the suture connected to the sling pubovaginally around each side of the patient's bladder neck; transposing the suture to a suprapubic position through the patient's subcutaneous tissue and out through the patient's skin; threading the suture through the tension device; tightening the tension of the suture until a desired level of tension support is achieved; and at least temporarily fixing the suture at the desired level of tension support with the tension device. The step of transposing is preferably accomplished at least in part using a percutaneous, incision-free needle.

The method may further comprise the step of, releasing one limb of the looped suture to disengage the suture from the sling, once fibroblast interposition and collagen deposition is at least partially achieved.

The sling of the method is preferably absorbable, synthetic, latex-free and may comprise one or more absorbable materials selected from a group consisting of chromic gut, polyglactin, polydioxanone, and combinations thereof. The sling may be fibrogenic and is preferably adapted to be absorbed in about 90 days. The monofilament suture of the method is preferably looped and comprises one or both prolene and nylon. The sling and suture may be prefabricated and preferably do not require physician reconstitution.

BRIEF DESCRIPTION OF THE DRAWINGS

Other objects, features and advantages will occur to those skilled in the art from the following description of the preferred embodiments and the accompanying drawings in which.

DETAILED DESCRIPTION OF THE PREFERRED EMBODIMENTS AND METHODS

The implantable system of the invention for managing urinary incontinence features a latex-free, synthetic sling made entirely of absorbable materials of which at least one of the materials is adapted to stimulate fibroblast interposition; and a looped monofilament suture that is adapted to be transposed to the suprapubic position, supported by an external adjustable tension device, and connected to the sling. The sling is adapted to promote increased rigidity of the anterior vaginal wall and improved integrity of the sphincteric mechanism.

Figure 1:
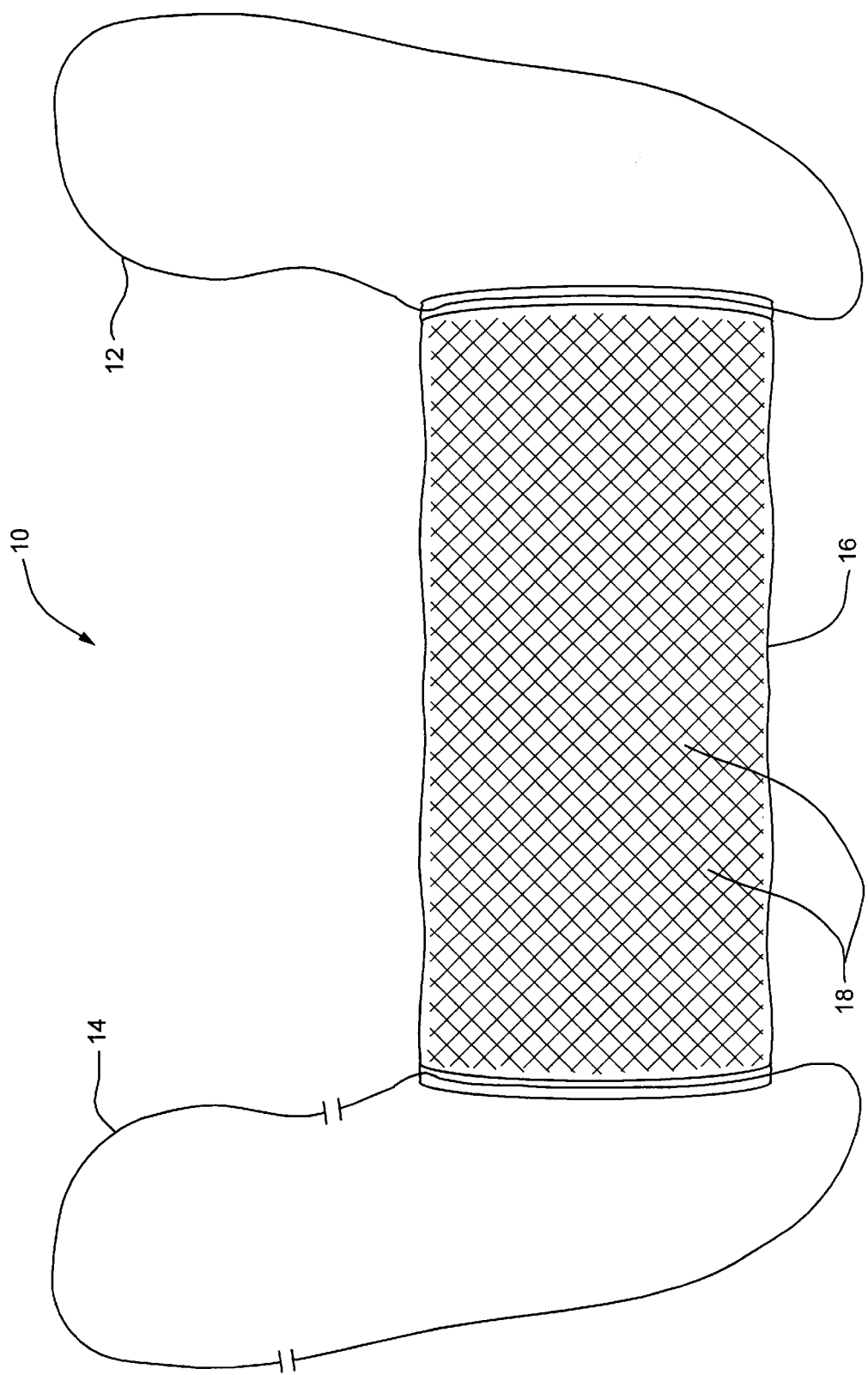
FIG. 1 is a front view of the preferred embodiment of the sling and sutures of the invention.

A preferred embodiment of the absorbable pubovaginal sling system for surgical management of urinary incontinence is shown in FIG. 1 and generally referred to as device 10. Device 10 generally comprises: a latex-free, synthetic sling 16 made entirely of absorbable materials of which at least one of the materials is adapted to stimulate fibroblast interposition; and a monofilament suture 12/14 that is adapted to be transposed to the suprapubic position. The system preferably further comprises an external adjustable tension device 20 (FIGS. 2 and 4) that is connected to suture 12/14 and is adapted to support sling 16.

Although other materials may be used, one or more of the absorbable materials of sling 16 is preferably selected from a group consisting of chromic gut, polyglactin, polydioxanone, and combinations thereof. The monofilament suture 12/14 is preferably looped and may comprise, but is not necessarily limited to, prolene and/or nylon.

Sling 16 and suture 12/14 may be prefabricated and preferably do not require physician reconstitution. The preferred size is 2×6 cm, although other variable dimensions may be used or otherwise required. Sling 16 is fibrogenic and preferably is braided or woven with a plurality of fenestrations 18 to allow in growth of fibroblasts and deposition of collagen. Sling is adapted to be absorbed at a slow rate. The preferred period of absorption is about 90 days.

Figure 3:
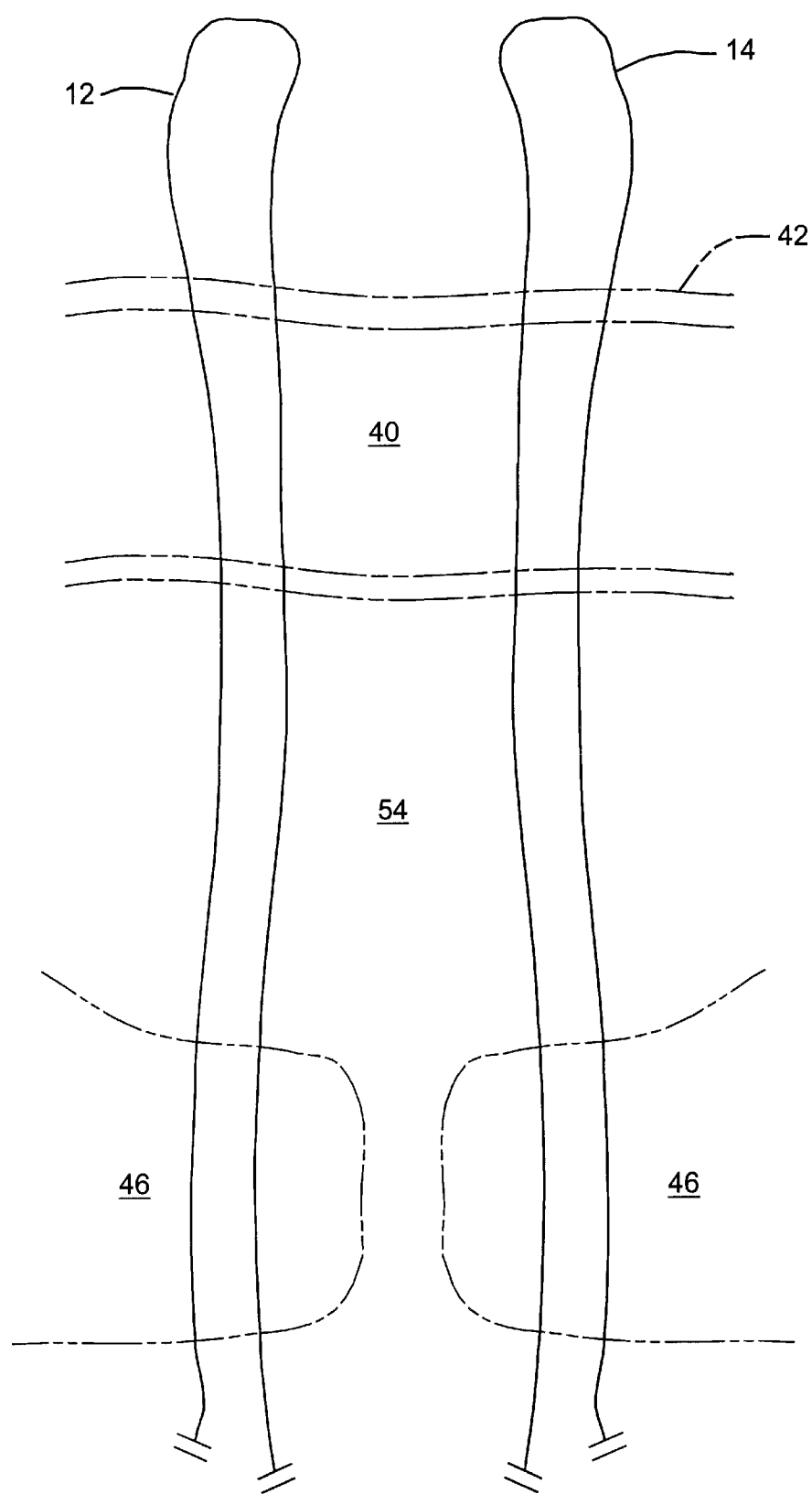
FIG. 3 is a cross-sectional view of the sling and sutures of the invention showing the percutaneous, incision-free transferal of the suprapubic suspension suture implanted according to the method of the invention.
Figure 4A:
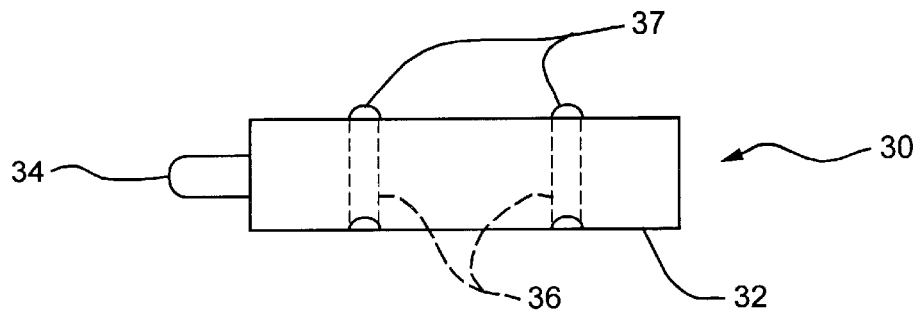
FIG. 4A is a side view of the preferred embodiment of the external tension adjusting device of the system of the invention in a relaxed, closed position.
Figure 4B:
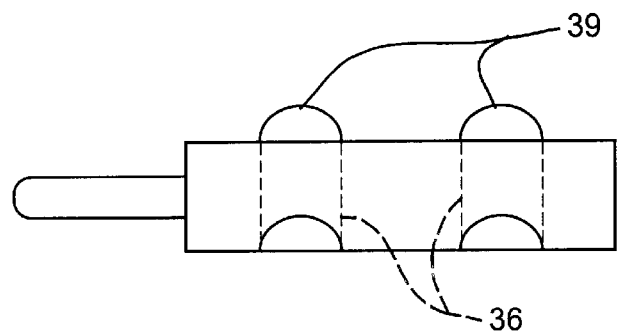
FIG. 4B is a side view of the external tension adjusting device shown in FIG. 4A in a tight, stretched position.
Figure 4C:
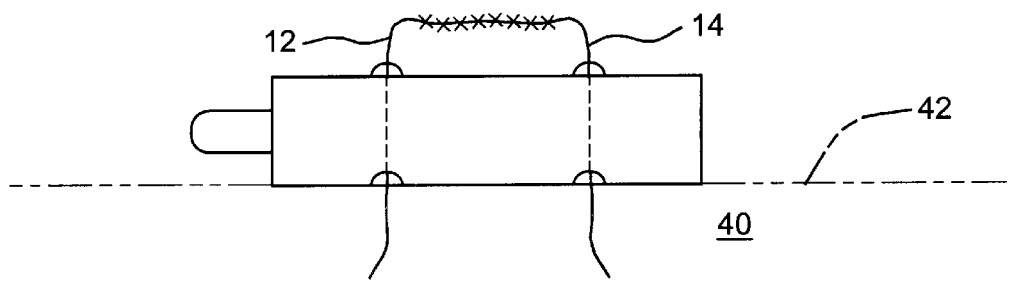
FIG. 4C is a side view of the external tension adjusting device shown in FIG. 4B with the sutures secured over the anchoring mechanism.

As shown in FIG. 3, suture 12/14 is adapted to pass through a patient's subcutaneous tissue 54 and skin layer 14 to connect to external adjusting device 20 located on the skin surface 42. External adjusting device 30 comprises one or more apertures 36 (FIGS. 4A–4C) through which suture 12/14 is passed and secured at an adjustable tension (FIG. 4A). External adjusting device 30 comprises anchoring mechanism 32 and adjuster 34. The tension of suture 12/14 may be readjusted by opening the apertures 36 of external adjusting device 30 to stretch and tighten suture 12/14 (FIG. 4B) and then closing the apertures 36 to secure the suture at the readjusted tension (FIG. 4C). The two suture ends 12/14 are secured, preferably by tying the ends to each other, above anchoring mechanism 32. The adjusting device 30 is shown in a relaxed, closed position in FIGS. 4A and 4B and in an open, tight, stretched position in FIG. 4B.

Figure 2:
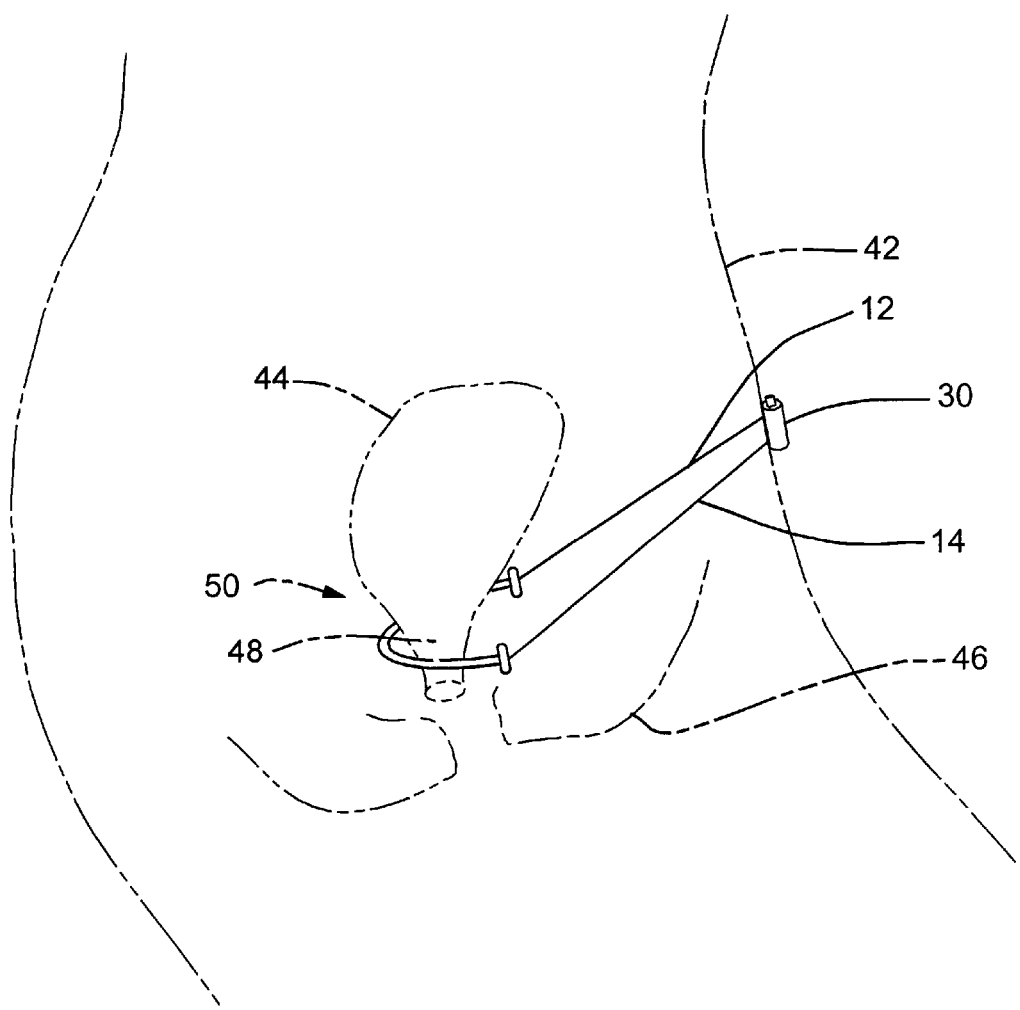
FIG. 2 is a cross-sectional side view of the preferred embodiment of the system of the invention implanted in a surgical position according to the method of the invention.

A preferred method of the invention for surgically managing urinary incontinence in a patient is generally shown in FIG. 2. The method generally comprises the steps of: providing one or more pubovaginal slings 16; providing one or more monofilament sutures 12/14 that is connected to sling 16 and is adapted to be transposed to a suprapubic position above the symphysis pubis 46; providing one or more external adjustable tension devices 30; implanting the sling and sutures by passing suture 12/14 pubovaginally around each anterior portion 50 of the patient's bladder neck 48; transposing suture to a suprapubic position above the symphysis pubis through the patient's subcutaneous tissue 54 and out through the patient's skin 40; threading suture 12/14 through tension device 30; tightening the tension of suture 12/14 until a desired level of tension support is achieved; and at least temporarily fixing suture 12/14 at the desired level of tension support by at least partially closing apertures 36 of tension device 30. The step of transposing is preferably accomplished in part using a percutaneous, incision-free needle.

Pulling on adjuster 34 enlarges the openings 39 through apertures 36. Releasing or pushing adjuster 34 causes apertures 36 to shrink to at least partially close openings 37 thus trapping sutures 12/14 within external adjusting device 30. The action of adjuster 34 may be achieved using various means including, but not limited to: a spring-loaded mechanism, elasticized components that stretch and give according to the tension placed on adjuster 34, or a tongue and groove design in which adjuster 34 acts as release or catch. Once fibroblast interposition and collagen deposition are at least partially achieved, the external adjusting device and the suture may be removed by releasing one limb of the looped suture to disengage the suture from the sling.

The sling material is characterized by delayed absorption/degradation, which allows for ample in growth of fibroblasts and collagen deposition. The sling material is prosthetic, synthetic and absorbable. It is not derived from a human or animal source and delivers no immune risk to the recipient. The components are preferably selected from a group consisting of, chromic gut, polyglactin, polydioxanone, and combinations thereof. The absorbable sling material is adapted to provide increased rigidity to the anterior vaginal wall and improve the integrity of the sphincteric mechanism.

The sling is preferably connected to a looped, transferable number one monofilament suture preferably made from prolene and/or nylon. The suspension loop interaction permits the bladder to fibrose against the posterior wall of the symphysis pubis. The fibrotic process maintains the bladder in a high retropubic position while the sling strengthens and supports the bladder neck. The fibrotic deposition between the anterior bladder wall and the posterior surface of the symphysis pubis will be sufficient to support the bladder location in a high retropubic position. The fibrosis scar tissue will replace the suspending suture as the primary support for the bladder.

The sling system is preferably single use, latex free and stimulates fibroblast interposition. The fibrotic ingrowth will strengthen the vaginal wall directly beneath the mid urethra/bladder neck/sphincteric mechanism.

Although specific features of the invention are shown in some drawings and not others, this is for convenience only as some feature may be combined with any or all of the other features in accordance with the invention.

Other embodiments will occur to those skilled in the art and are within the following claims:

What is claimed is:

1. An absorbable pubovaginal sling system for surgical management of a patient's urinary incontinence that is adapted to be implanted to promote increased rigidity of the anterior vaginal wall and improved integrity of the sphincteric mechanism, comprising:

one or more latex-free, synthetic slings made entirely of absorbable materials of which at least one of said materials is adapted to stimulate fibroblast interposition;

one or more monofilament sutures that is adapted to be connected to said sling proximate a bladder neck and transposed to a suprapubic position and is configured to extend through said patient's subcutaneous tissue and outer layer of skin; and one or more means for fixing said suture at a desired tension, wherein said means for fixing is adapted to be seated on the outside of the patient's body against the patient's abdomen, wherein said means for fixing engages said sutures, and wherein said means for fixing comprises a means for releasably adjusting said tension of said sutures from the outside of the patient's body.

2. The sling system of claim 1, wherein one or more of said absorbable materials is selected from a group consisting of chromic gut, polyglactin, polydioxanone.

3. The sling system of claim 1, wherein said monofilament suture is looped and comprises one or both prolene and nylon.

4. The sling system of claim 1, wherein said sling and suture are prefabricated and do not require physician reconstitution.

5. The sling system of claim 1, wherein said sling is either braided or woven with a plurality of fenestrations to allow ingrowth of fibroblasts.

6. The sling system of claim 1, wherein said sling is fibrogenic and is adapted to be absorbed at a slow rate.

7. The sling system of claim 6, wherein said sling is adapted to be absorbed in about 90 days.

8. The sling system of claim 1, wherein said means for fixing comprises one or more apertures through which said suture is passed and secured at an adjustable tension.

9. The sling system of claim 1, wherein said means for fixing comprises one or more apertures whereby said tension of said suture is releasably adjusted by opening said aperture of said means for fixing to stretch and tighten, or loosen, the tension of suture and then closing said aperture of the means for fixing to secure the suture at said readjusted tension.

10. A method for surgically managing urinary incontinence in a patient, comprising the steps of, providing one or more pubovaginal slings;

providing one or more monofilament sutures that is connected to said sling and is adapted to be transposed to a suprapubic position;

providing one or more external adjustable tension devices;

passing said suture connected to said sling pubovaginally around each side of the patient's bladder neck;

transposing said suture to a suprapubic position through the patient's subcutaneous tissue and out through the patient's skin;

threading said suture through said tension device;

tightening the tension of said suture until a desired level of tension support is achieved; and at least temporarily fixing said suture at said desired level of tension support with said tension device.

11. The method of claim 10, further comprising the step of, releasing one limb of said looped suture to disengage said suture from said sling, once fibroblast interposition and collagen deposition is at least partially achieved.

12. The method of claim 10, wherein said step of transposing is accomplished in part using a percutaneous, incision-free needle.

13. The method of claim 10, wherein said sling is absorbable, synthetic, latex-free and comprises one or more absorbable materials selected from a group consisting of chromic gut, polyglactin, polydioxanone.

14. The method of claim 10, wherein said monofilament suture is looped and comprises one or both prolene and nylon.

15. The method of claim 10, wherein said sling and suture are prefabricated and do not require physician reconstitution.

16. The method of claim 10, wherein said sling is fibrogenic and is adapted to be absorbed in about 90 days.

* * * * *